US012758659B2

(12) United States Patent
Yang et al.

(10) Patent No.: US 12,758,659 B2
(45) Date of Patent: Oct. 13, 2026

(54) PSMA INHIBITOR, COMPOUND AND APPLICATION

(71) Applicant: PEKING UNIVERSITY FIRST HOSPITAL, Beijing (CN)

(72) Inventors: Xing Yang, Beijing (CN); Zhi Yang, Beijing (CN); Zhen Xi, Beijing (CN); Futao Liu, Beijing (CN); Xiaojiang Duan, Beijing (CN); Ning Zhang, Beijing (CN)

(73) Assignee: PEKING UNIVERSITY FIRST HOSPITAL, Beijing (CN)

(*) Notice: Subject to any disclaimer, the term of this patent is extended or adjusted under 35 U.S.C. 154(b) by 970 days.

(21) Appl. No.: 18/019,758

(22) PCT Filed: Jan. 21, 2020

(86) PCT No.: PCT/CN2020/073347
§ 371 (c)(1),
(2) Date: Aug. 18, 2023

(87) PCT Pub. No.: WO2020/156345
PCT Pub. Date: Aug. 6, 2020

(65) Prior Publication Data

US 2023/0414794 A1 Dec. 28, 2023

(30) Foreign Application Priority Data

Feb. 3, 2019 (CN) ........................ 201910108684.X
Mar. 19, 2019 (CN) ........................ 201910208822.1

(51) Int. Cl.

| | |
|---|---|
| ***A61K 51/04*** | (2006.01) |
| ***A61K 45/06*** | (2006.01) |
| ***C07B 59/00*** | (2006.01) |
| ***C07C 275/16*** | (2006.01) |
| ***C07D 311/18*** | (2006.01) |

(52) U.S. Cl.
CPC .......... *A61K 51/0402* (2013.01); *A61K 45/06* (2013.01); *C07B 59/001* (2013.01); *C07C 275/16* (2013.01); *C07D 311/18* (2013.01); *A61K 2123/00* (2013.01); *C07B 2200/05* (2013.01)

(58) Field of Classification Search
None
See application file for complete search history.

(56) References Cited

FOREIGN PATENT DOCUMENTS

WO 2017027870 A1 2/2017

OTHER PUBLICATIONS

Yang et al (J Med Chem, 2016, 59(1): 206-218). (Year: 2016).*
International search report issued for counterpart Chinese Patent Application No. PCT/CN2020/073347 mailed on Apr. 14, 2020.
Xing Yang et al.,"[18F] Fluorobenzoyllysinepentanedioic Acid Carbamates: New Scaffolds for Positron Emission Tomography (PET) Imaging of Prostate-Specific Membrane Antigen(PSMA)"Journal of Medicinal Chemistry, vol. 59, Dec. 31, 2015.
First Office Action and search report issued on Sep. 9, 2019 for counterpart Chinese Patent Application No. 201910108684.X.
Second Office Action issued on Oct. 16, 2019 for counterpart Chinese patent application No. 201910108684.X .
Supplementary search report issued on Feb. 3, 2019 for counterpart Chinese patent application No. 201910108684.X.
Vojtech Klusak et al., Reaction Mechanism of Glutamate Carboxypeptidase II Revealed by Mutagenesis, X-ray Crystallography, and Computational Methods, Biochemistry, 48(19) 4126-38, 2009.
Haofan et al., Bioisosterism of urea-based GCPII inhibitors: Synthesis and structure-activity relationship studies, Bioorganic &Medicinal Chemistry Letters, 20:392-397, 2010.
Steve Y. Cho et al., Biodistribution, Tumor Detection, and Radiation Dosimetry of 18F-DCFBC, a Low-Molecular-Weight Inhibitor of Prostate-Specific Membrane Antigen, in Patients with Metastatic Prostate Cancer, Journal of Nuclear Medicine, 53:1883-1891, 2012.
Martin G. Pomper et al., 11C-MCG: Synthesis, Uptake Selectivity, and Primate PET of a Probe for Glutamate Carboxypeptidase II (NAALADase), Molecular Imaging, 1:96-101, 2002.
A. P. Kiess et al., Prostate-specific membrane antigen as a target for cancer imaging and therapy, The Quarterly Journal of Nuclear Medicine and Molecular Imaging, 59:241-68, 2015.
First Office Action and search report issued on Sep. 23, 2022 for counterpart Chinese Patent Application No. 201911408554.4.
Search report issued on Sep. 23, 2022 for counterpart Chinese Patent Application No. 201911408554.4.

* cited by examiner

*Primary Examiner* — Celeste A Roney
(74) *Attorney, Agent, or Firm* — LOZA & LOZA, LLP; Michael Fedrick

(57) ABSTRACT

The present disclosure belongs to the technical field of biomedicine, and specifically relates to a PSMA inhibitor, compound and use thereof. The PSMA inhibitors having a novel core structure provided in the present disclosure has a wide range of potential applications.

15 Claims, 6 Drawing Sheets

PSMA INHIBITOR, COMPOUND AND APPLICATION

CROSS-REFERENCE TO RELATED APPLICATIONS

This application is the U.S. national stage of International Patent Application No. PCT/CN2020/073347, filed on Jan. 21, 2020, which claims the benefit of priority under 35 U.S.C. § 119 from Chinese Patent Application No. 2019102088221, filed on Mar. 19, 2019, and from Chinese Patent Application No. 201910108684X, filed on Feb. 3, 2019. The disclosures of the foregoing applications are incorporated herein by reference in their entireties.

TECHNICAL FIELD

The present disclosure belongs to the technical field of biomedicine, and more particularly, relates to a compound having a core structure of PSMA inhibitors, a PSMA inhibitor obtained therefrom, a PSMA inhibitor compound having a functional group, and their use.

BACKGROUND

Prostate cancer is one of the most common malignant tumors in men, with the highest incidence in Europe and the United States for years. Although the incidence of prostate cancer in China is lower than that in Europe and the United States, it has seen a considerable increase in China in recent years with the advent of an aging society and westernization of lifestyle. Meanwhile, among prostate cancer patients in China, the proportion of intermediate- and high-risk patients and advanced-stage patients is significantly higher than that in Europe and the United States. Since the effectiveness of tumor treatment is closely related to the stage of the disease, the prostate cancer mortality rate in China remains at a high level. With the advances in medical science, currently only a small percentage of prostate cancers are fatal (e.g., late-stage castration-resistant types), so accurate staging and monitoring of this cancer is critical to optimization of the treatment.

Currently recommended imaging examinations include multiparametric magnetic resonance imaging (mpMRI), CT (computed tomography), Bone Scan, PET/CT, etc. However, the existing conventional imaging examinations have limitations. For example, judgment of lymph node metastasis and bone metastasis in medium- and high-risk prostate cancer patients and imaging monitoring of patients with biochemical relapse have been important for diagnosis but remained difficult. The advancement of molecular imaging technology has brought fresh hope for individualized and precise diagnosis and treatment of prostate cancer. To date, a large number of molecular probes for prostate cancer have been applied in the clinic and benefited patients. Among them, the research on specific molecular probes targeting the prostate-specific membrane antigen (PSMA) has made a major breakthrough in recent years and has been rapidly translated into clinical practice, showing promising application potentials in diagnosis, staging, restaging, relapse monitoring and targeted radiation therapy of prostate cancer.

PSMA is a membrane protein with a catalytic function, which was first discovered in the nervous system and named GCPII (glutamate carboxypeptidase II). PSMA is normally expressed in prostate epithelial cells and also in salivary glands, kidney, duodenum and other organs. The expression of neovascular PSMA is significantly higher in prostate cancer and some solid tumors (e.g. colon cancer, breast cancer, kidney cancer and bladder cancer), and is significantly correlated with the degree of tumor differentiation, metastatic tendency of the tumor, and sensitivity of the tumor to hormonal therapy. Studies have confirmed that PSMA is highly expressed in almost all prostate cancer tissues, and particularly strongly overexpressed in castration resistant and metastatic prostate cancers, making PSMA an ideal biomarker for highly sensitive and specific localization imaging of metastatic prostate cancer foci and for advanced nuclide targeted therapy. It has been reported that expression of PSMA is correlated with the malignancy degree of prostate tumors and post-operational relapse. PSMA has an important role in TMPRSS2: ERG fusion mutations, androgen receptor signaling, and chromosomal instability in tumor cells, which makes PSMA imaging a potential means of pre-assessment of tumor treatment.

Due to the importance of PSMA in the diagnosis and treatment of prostate cancer, antibody-based research was first conducted (monoclonal antibodies 7E11-C5.3, J591, etc.) and applied in imaging and targeted radiotherapy trials. Early research confirmed the feasibility of this approach, but antibodies have serious limitations as a routine clinical molecular imaging tool. Antibodies require a long in vivo metabolism time (typically 3-7 days) to reduce the circulating background to achieve adequate signal-to-noise ratio, and their size also limits their tumor penetration. In contrast, small-molecule imaging agents offer tremendous advantages in terms of clinical translation. Good small-molecule imaging agents can achieve rapid elimination of blood background signals, and allow patients to complete medication injection and high definition imaging within 1-2 hours with the aid of short half-life radionuclide ($^{11}C$, $^{68}Ga$, $^{18}F$, etc.). In addition, small molecules are less likely to be recognized and rejected by the immune system, and purification and quality control can be standardized, thereby ensuring safety and reproducibility during use.

Medicinal chemistry studies on PSMA have been focusing on its inhibitors. Researchers have tried to find medications for treatment of neurological disorders, and in 1996 and 2001 discovered multiple classes of inhibitors based on phosphate derivatives (Phosphonate) and urea derivatives (Urea). Early studies on PSMA inhibitors provided useful small-molecule tools for the development of efficient PSMA-targeting agents. In 2002, the Pomper lab at Johns Hopkins School of Medicine introduced for the first time a urea-based small-molecule inhibitor ( 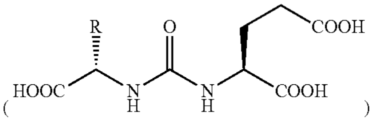 )

to prostate cancer-specific nuclear medicine imaging studies, and in 2012 reported the results of clinical trials of the first-generation $^{18}F$ imaging agent, confirming its accessibility and specificity (Molecular Imaging, 2002, 1, 96-101. Journal of Nuclear Medicine, 2012, 53, 1883-1891). The highly specific imaging of PSMA in prostate cancer has accelerated the progress of nuclide targeted therapy. A study in this area that began in 2013 in Germany showed that PSMA-guided Beta-Ray Nuclide $^{177}Lu$ targeted therapy against advanced castration-resistant prostate cancer demonstrated an effective control rate of as high as 80%, including about 23% cases achieving more than 80% reduction in the blood PSA index.

The choice of low-energy Beta-Ray Nuclide $^{177}$Lu for the nuclide targeted therapy balances efficacy and safety; each of the slow courses of therapy (2 months) gives time for high background normal organs such as kidney to recover, but also gives tumor cells a chance to further proliferate, mutate, and develop resistance. It was found in the experiments that about 20% of the cases showed no efficacy and many cases gradually failed to control the disease during treatment. The use of higher energy and highly cytotoxic Alpha-Ray nuclide $^{225}$AC and $^{213}$Bi needs targeting agents having higher specificity and in vivo metabolic profiles to avoid huge toxic side effects.

Since 2012, pharmacological research has started to dig and focus on the core issues in clinical translation such as metabolic kinetics, nuclide selection and optimization, and several improved urea-based molecules have been reported and undergone clinical trials in several countries, showing a great potential for application. However, because of the conserved structure of PSMA inhibitors, some minor changes to the core structure of urea-based inhibitors lead to a sharp decrease in binding constants (Bioorganic & Medicinal Chemistry Letters 20 (2010) 392-397). Hundreds of compounds with improvements on PSMA inhibitors have been reported in the literature, but only a few of the improved inhibitors exhibit a binding constant similar to that of urea-based inhibitors, and some of them are structurally unstable, leaving very few to have a real potential in application.

In contrast, unlike the extremely conserved core structure, researchers have found that PSMA inhibitors have little restriction on the choice of the R group. FIG. 1*a* and FIG. 1*b* illustrate the mechanism of the catalytic activity of PSMA (Biochemistry. 2009 May 19; 48(19): 4126-38), and it can be seen that the core structure responsible for the catalytic activity is the S1 pocket, S1' pocket and Zn catalytic site, while the functional groups connected to the S1 pocket have much less influence on the catalytic activity than the core structure has. This is also supported by a review for PSMA (The Quarterly Journal of Nuclear Medicine and Molecular Imaging, 2015; 59:241-68).

Among the many indexes for clinical applications of PSMA inhibitors, affinity is one of the most critical, as affinity determines the targeting of PSMA inhibitors, and in turn influences their application as a diagnostic or therapeutic agent. Therefore, development of a compound having an improved core structure will undoubtedly have an important scientific value and a bright prospect in a wide range of applications.

SUMMARY

The present disclosure provides a compound which is at least one of a compound having the structure of Formula I and a pharmaceutically acceptable salt thereof:

Formula I

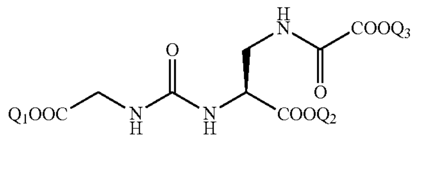

wherein $Q_1$, $Q_2$ and $Q_3$ are each independently H, a negative charge, a metal ion, or a protecting group.

According to the present disclosure, $Q_1$, $Q_2$ and $Q_3$ being a negative charge means forming a carboxylate anion. The metal ion includes any metal ion capable of attaching to a carboxylic acid, including but not limited to alkali metal ions such as sodium ion and potassium ion. The protecting group may be a conventional carboxylic acid-protecting group, such as a tert-butyl.

BRIEF DESCRIPTION OF DRAWINGS

The foregoing and other objectives, features and advantages of the present disclosure will become more apparent by a more detailed description of exemplary embodiments of the present disclosure in conjunction with the drawings.

DETAILED DESCRIPTION

Figure 1A:
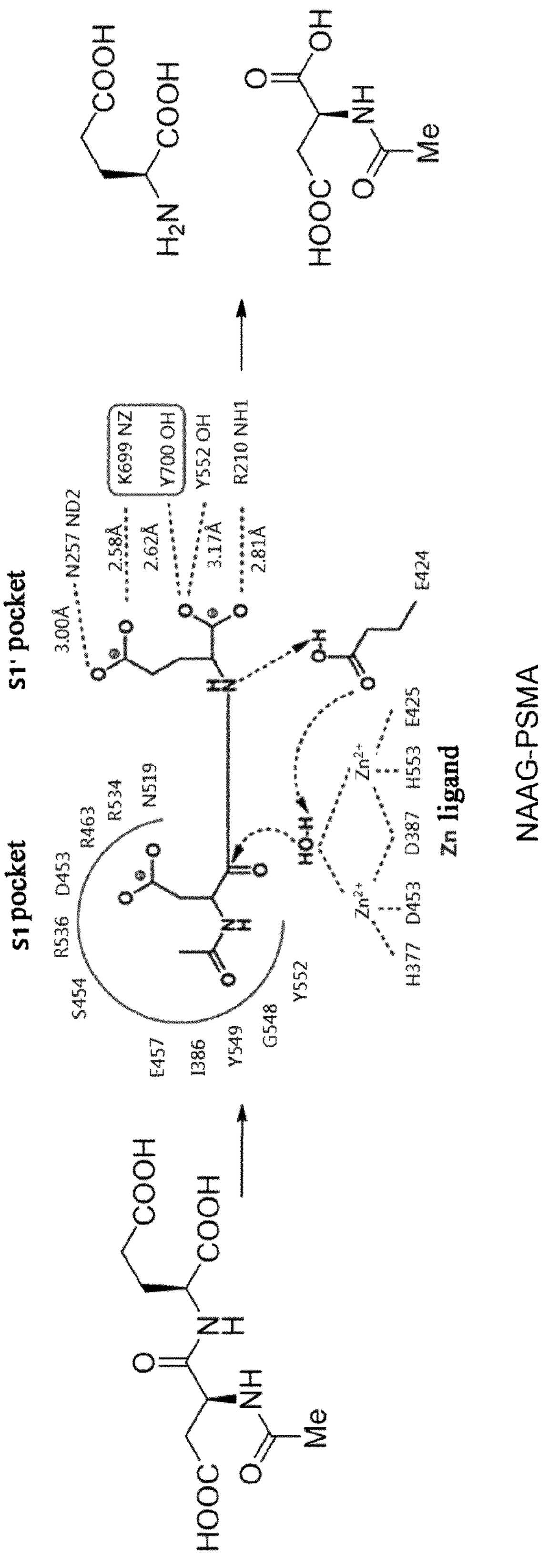
FIG. 1*a* and FIG. 1*b* illustrate the mechanism of the catalytic activity of PSMA.
Figure 1B:
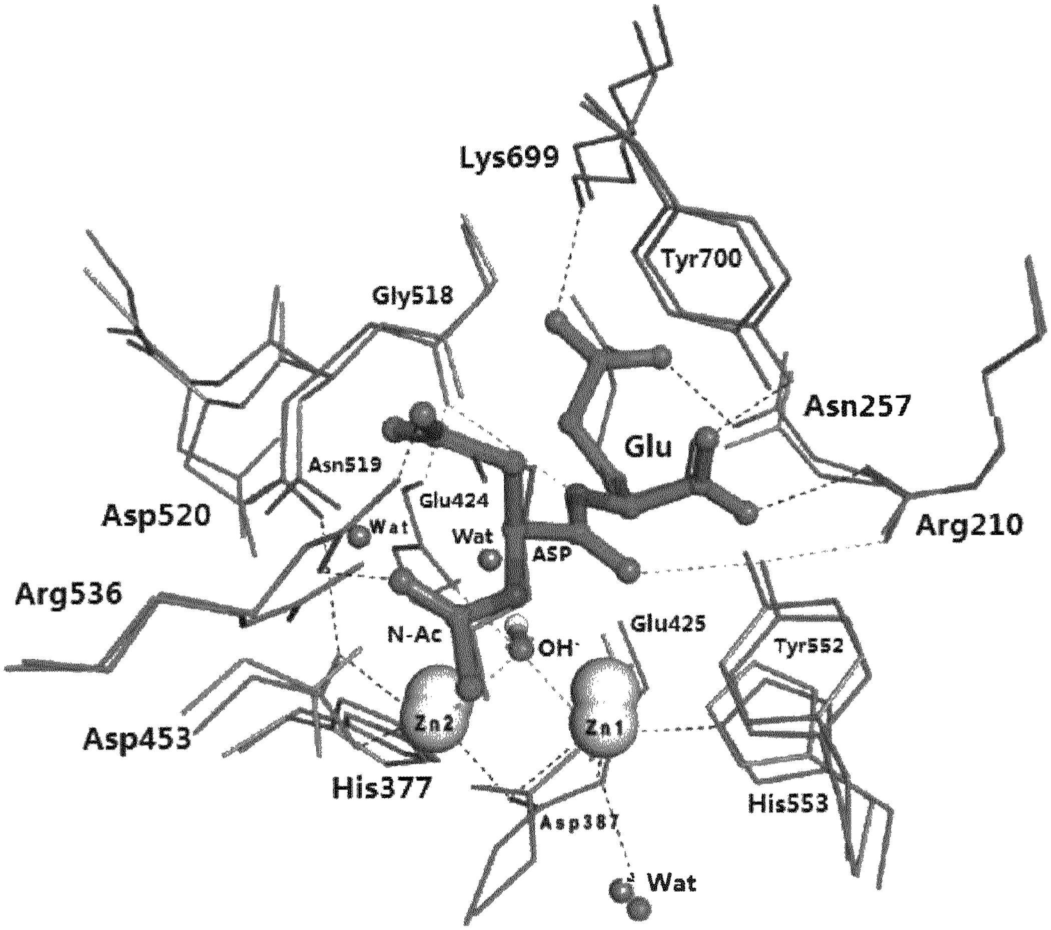

The present disclosure provides a compound which is at least one of a compound having the structure of Formula I and a pharmaceutically acceptable salt thereof:

Formula I

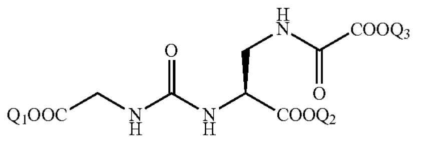

wherein $Q_1$, $Q_2$ and $Q_3$ are each independently H, a negative charge, a metal ion, or a protecting group.

According to the present disclosure, $Q_1$, $Q_2$ and $Q_3$ being a negative charge means forming a carboxylate anion. The metal ion includes any metal ion capable of attaching to a carboxylic acid, including but not limited to alkali metal ions such as sodium ion and potassium ion. The protecting group may be a conventional carboxylic acid-protecting group, such as a tert-butyl.

The compound having the structure of Formula I according to the present disclosure or a group derived therefrom (preferably, a monovalent group) can serve as a unit specifically recognizing PSMA and/or as a core structure of PSMA inhibitors. That is, from the compound having the structure of Formula I, other compounds can be derived to specifically recognize PSMA, using the compound having the structure of Formula I or a group derived therefrom as the recognition unit. Therefore, the compound having the structure of Formula I or a group derived therefrom becomes the core structure of these derived compounds functioning as a PSMA inhibitor.

The compound having the structure of Formula I according to the present disclosure or a group derived therefrom (preferably, a monovalent group) can be used to prepare an agent and/or medication for diagnosis and/or treatment of one or more types of tumors or cells expressing PSMA.

Since a compound having the structure of Formula I can serve as a core structure for PSMA inhibitors, when it is modified with a diagnostic and/or therapeutic function unit, the modified form can serve as a corresponding diagnostic and/or therapeutic agent and/or medication.

The present disclosure does not specifically limit the specific forms of the diagnosis and therapy, which depend entirely on the modification unit.

According to some embodiments of the present disclosure, the diagnosis is in the form of optical imaging and/or nuclide imaging. The nuclide imaging includes but not limited to PET imaging and/or SPECT imaging.

According to some embodiments of the present disclosure, the therapy comprises radiotherapy.

According to some embodiments of the present disclosure, the medication comprises at least one of a chemical medication, a nucleic acid medication and a protein medication. The nucleic acid medication includes but not limited to an siRNA medication. The definition and scope of the medication are consistent with conventional criteria in the field of pharmaceutics.

Furthermore, the present disclosure provides a PSMA inhibitor which is a derivative of a compound having the structure of Formula I, and includes a group derived from the compound having the structure of Formula I as a core structure to specifically recognize PSMA; wherein the group derived from the compound having the structure of Formula I is a group formed after one hydrogen atom on the carbon atom marked with * in Formula I is substituted, and after the hydrogen atom is substituted, the carbon atom marked with * forms an S-chiral conformation.

Formula I

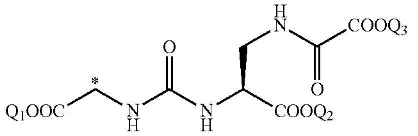

wherein $Q_1$, $Q_2$ and $Q_3$ are each independently H, a negative charge, a metal ion, or a protecting group.

Another aspect of the present disclosure provides a compound which is at least one of a compound having the structure of formula II and a pharmaceutically acceptable salt thereof.

Formula II

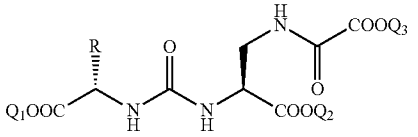

wherein $Q_1$, $Q_2$ and $Q_3$ are each independently H, a negative charge, a metal ion, or a protecting group; and R is a functional group.

Since the compounds of Formula II share a common core structure of PSMA inhibitors, the specific choice of the R group attached to the core structure does not affect their use as a PSMA inhibitor, and R is not particularly limited in the present disclosure.

According to some embodiments of the present disclosure, the functional group R is a group having one of tracing, delivery, imaging and therapeutic functions.

In some embodiments, the functional group R is selected from the group consisting of a radionuclide-containing group, an optical imaging and/or optical therapeutic group, a group having a magnetic resonance effect, an immunological group, a medication, and a group formed by a delivery system thereof.

In some embodiments, the medication comprises at least one of a chemical medication, a nucleic acid medication, and a protein medication; the nucleic acid medication includes but not limited to an siRNA medication; and the definition and scope of the medication is consistent with conventional criteria in the field of pharmaceutics.

In some embodiments, the radionuclide includes but not limited to at least one of radionuclides for PET imaging, SPECT imaging, and radiotherapy; and in some examples, the radionuclide is selected from the group consisting of $^{18}$F, $^{11}$C, $^{68}$Ga, $^{124}$I, $^{89}$Zr, $^{64}$Cu, $^{86}$Y, $^{99m}$Tc, $^{111}$In, $^{123}$I, $^{90}$Y, $^{125}$I, $^{131}$I, $^{177}$Lu, $^{211}$At, $^{153}$Sm, $^{186}$Re, $^{188}$Re, $^{67}$Cu, $^{212}$Pb, $^{225}$Ac, $^{213}$Bi, $^{212}$Bi, $^{212}$Pb, and $^{67}$ Ga. When R is a radionuclide-containing group, R typically includes a chelating moiety and a linking moiety, wherein the chelating moiety is used to chelate the radionuclide, and the linking moiety is used to form a linkage with the core structure in Formula II.

In some embodiments, the optical imaging and/or optical therapeutic group preferably comprises a group formed from an agent for infrared imaging, photoacoustic imaging, photodynamic therapy or photothermal therapy.

According to some embodiments of the present disclosure, the compound is at least one of a compound having the structure of Formula III and a pharmaceutically acceptable salt thereof.

Formula III

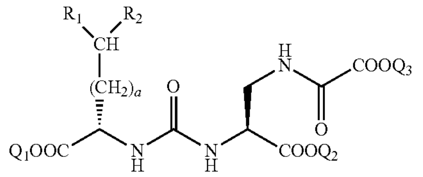

wherein $Q_1$, $Q_2$ and $Q_3$ are each independently H, a negative charge, a metal ion, or a protecting group;

a is an integer selected from 0, 1, 2, 3, 4 or 5;

$R_1$ and $R_2$ are each independently H, a linear or branched $C_1$-$C_4$ alkyl, or a group having the structure of Formula IV; in some embodiments, one of $R_1$ and $R_2$ is a group having the structure of Formula IV; in at least one example, when one of $R_1$ and $R_2$ is a group having the structure of Formula IV, the other one is H;

Formula IV

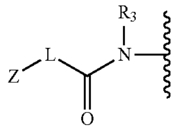

in Formula IV, $R_3$ is H, or a linear or branched $C_1$-$C_4$ alkyl;

L is a chemical bond, or a linear or branched $C_1$-$C_4$ alkyl;

Z is selected from the group consisting of a group containing at least one nuclide suitable for nuclide imaging and/or radiotherapy, and a group containing at least one photosensitive dye suitable for optical imaging and/or photodynamic therapy.

In the present disclosure, "a group containing at least one nuclide suitable for nuclide imaging and/or radiotherapy, and a group containing at least one photosensitive dye suitable for optical imaging and/or photodynamic therapy" mean that Z may be the nuclide or photosensitive dye itself, or may contain other groups for attaching (e.g., chelating) the nuclide, or other groups for attaching or modifying the photosensitive dye, etc.

In the case of the group containing at least one photosensitive dye suitable for optical imaging, Z may be selected from a variety of photosensitive dyes conventionally used in the art, such as fluorescent dyes, and specifically, Z may be selected from the group consisting of a substituted or unsubstituted $C_6$-$C_{16}$ aryl and a substituted or unsubstituted $C_3$-$C_{16}$ heteroaryl, wherein the substitution may be at least one of halogen substitution, linear or branched $C_1$-$C_4$ alkyl substitution, amino substitution and carbonyl substitution, where the carbonyl substitution means that a carbon atom is attached to an oxygen atom by a double bond to form a carbonyl group.

In some embodiments, the substituted or unsubstituted $C_6$-$C_6$ aryl is a substituted or unsubstituted $C_6$-$C_{12}$ aryl, for example phenyl or naphthyl. In some embodiments, the substituted or unsubstituted $C_3$-$C_{16}$ heteroaryl is a substituted or unsubstituted $C_5$-$C_{12}$ heteroaryl with one or more heteroatoms each selected from nitrogen (N), oxygen (O) and sulfur (S). In the above groups, the substitution comprises at least one of halogen substitution, linear or branched $C_1$-$C_4$ alkyl substitution, amino substitution and carbonyl substitution.

According to one or more embodiment of the present disclosure, Z is a substituted $C_6$-$C_{12}$ aryl, wherein the substituent is at least one of halogen and a linear or branched $C_1$-$C_4$ alkyl.

According to a more specific embodiment of the present disclosure, Z is a halogen-substituted $C_6$-$C_{10}$ aryl, wherein the halogen may be iodine (I).

According to another embodiment of the present disclosure, Z is a $C_6$-$C_{10}$ fused ring heteroaryl substituted with an amino group, wherein the fused ring is formed from phenyl and a lactone.

Specifically and preferably, Z is a group of Formula V or Formula VI.

Formula V

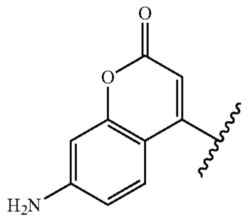

Formula VI

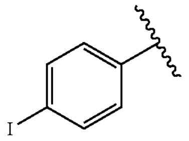

According to the embodiment of the present disclosure, the nuclide suitable for nuclide imaging and/or radiotherapy is selected from the group consisting of $^{18}F$, $^{11}C$, $^{68}Ga$, $^{124}I$, $^{89}Zr$, $^{64}Cu$, $^{89}Y$, $^{99m}Tc$, $^{111}In$, $^{123}I$, $^{90}Y$, $^{125}I$, $^{131}I$, $^{177}Lu$, $^{211}At$, $^{125}Sm$, $^{186}Re$, $^{188}Re$, $^{67}Cu$, $^{212}Pb$, $^{225}Ac$, $^{213}Bi$, $^{212}Bi$, $^{212}Pb$, and $^{67}Ga$.

According to the embodiment of the present disclosure, the compound having the structure of Formula III is selected from the group consisting of:

Compound S1

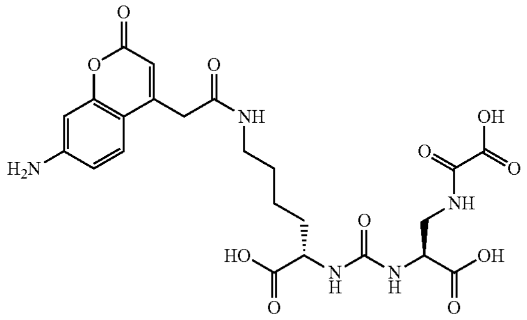

Compound S2

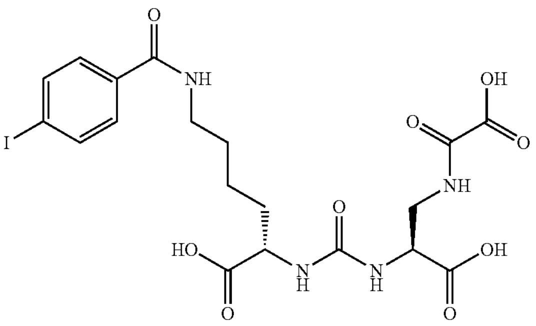

-continued

Compound S3

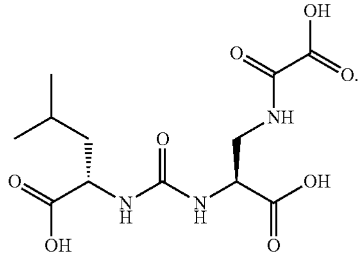

Figure 2:
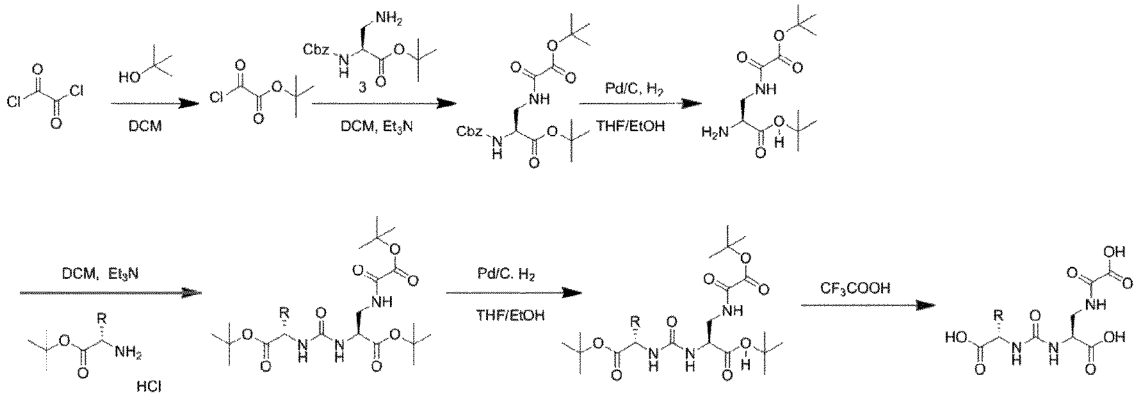
FIG. 2 illustrates a synthetic route for a compound of the present disclosure.
Figure 3:
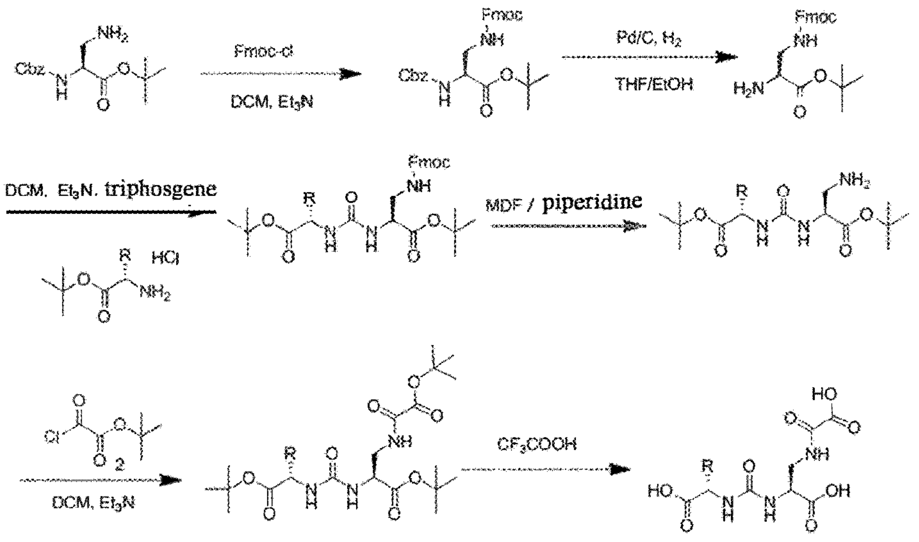
FIG. 3 illustrates another synthetic route for a compound of the present disclosure.

The above PSMA inhibitors and compounds according to the present disclosure can all be prepared by conventional synthesis methods in organic chemistry, for example, by the synthetic route shown in FIG. 2, or by the synthetic route shown in FIG. 3.

At least one of the above PSMA inhibitors and compounds according to the present disclosure can be used to prepare agents and/or medications for diagnosis and/or treatment of one or more types of tumors or cells expressing PSMA.

The description of the form of diagnosis and treatment, and the descriptions of the medications are as previously described and will be omitted here.

In the present disclosure, the one or more types of tumors or cells expressing PSMA are selected from the group consisting of prostate tumors or cells, metastatic prostate tumors or cells, lung tumors or cells, kidney tumors or cells, liver tumors or cells, glioblastomas, pancreatic tumors or cells, bladder tumors or cells, sarcomas, melanomas, breast tumors or cells, colon tumors or cells, germ cells, pheochromocytoma, esophageal tumors or cells, and gastric tumors or cells.

The one or more types of tumors or cells expressing PSMA described in the present disclosure may be in vitro, in vivo, or ex vivo.

The present disclosure also provides a method for imaging or treating one or more types of tumors or cells expressing the prostate-specific membrane antigen (PSMA), comprising contacting the tumors or cells with an effective amount of a PSMA inhibitor, and optionally generating an image, wherein the PSMA inhibitor is the aforementioned PSMA inhibitor compound.

The descriptions of the one or more types of tumors or cells expressing PSMA are as previously described and will be omitted here.

Definitions

Although the following terms for various compounds are believed as well understood by those ordinarily skilled in the art, the following definitions are set forth to facilitate interpretation of the subject matter of the present disclosure. These definitions are intended to supplement and illustrate, rather than preclude, the understanding of those ordinarily skilled in the art after reading the present disclosure.

As used herein, whether or not preceded by the term "optionally", the terms "substitution", "substituted" and "substituent" refers to, as understood by those skilled in the art, changing one functional group to another functional group while maintaining the chemical valence of all atoms. When more than one position in any given structure may be substituted by more than one substituent selected from a specified group, the substituents at the positions may be the same or different from each other. Moreover, the substituents may be further substituted.

As used herein, the term "derived" means that a class of compounds contains a structure of another class of compounds or another compound, but does not require that the "derived" compounds are prepared directly from another class of compounds or from another compound. For example, "other compounds may be derived from a compound having the structure of Formula I" means that said other compounds contain a structural unit formed from the compound having the structure of Formula I, but does not require that said other compounds must be prepared from the compound having the structure of Formula I as an intermediate.

Unless otherwise specified, the term "alkyl" by itself or as part of another substituent means a linear or branched, acyclic or cyclic hydrocarbon group or a combination thereof, which may be fully saturated, monounsaturated or polyunsaturated. It includes, but is not limited to, methyl, ethyl, n-propyl, isopropyl, n-butyl, isobutyl, sec-butyl, or tert-butyl. In some embodiments, alkyl is a $C_1$-$C_4$ alkyl, examples of which include methyl (Me), ethyl (Et), propyl (including n-propyl, iso-propyl (i-Pr), cyclopropyl (c-Pr)), butyl (including n-butyl (n-Bu), iso-butyl (i-Bu), sec-butyl (s-Bu), tert-butyl (t-Bu), cyclobutyl (c-Bu)), etc.

Unless otherwise specified, the term "aryl" means an aromatic hydrocarbon substituent, which may be a monocyclic, fused polycyclic, or covalently linked polycyclic group (e.g. one to three rings). The term "heteroaryl" refers to an aryl group (or ring) comprising at least one heteroatom selected from N, O and S. The heteroaryl group may be attached to other part of a molecule via a carbon atom or a heteroatom.

In the present disclosure, the term "halogen" includes F, Cl, Br, and I.

Preferred embodiments of the present disclosure will be described in greater detail below. Although preferred embodiments of the present disclosure are described below, it should be understood that the present disclosure may be implemented in various forms and should not be limited to the embodiments set forth herein.

Where specific conditions are not indicated in the following Examples, they are carried out under conventional conditions or those recommended by the manufacturers. The reagents or instrument used, where their manufacturers are not specified, are conventional products available commercially.

Example 1 and Example2

Figure 4:
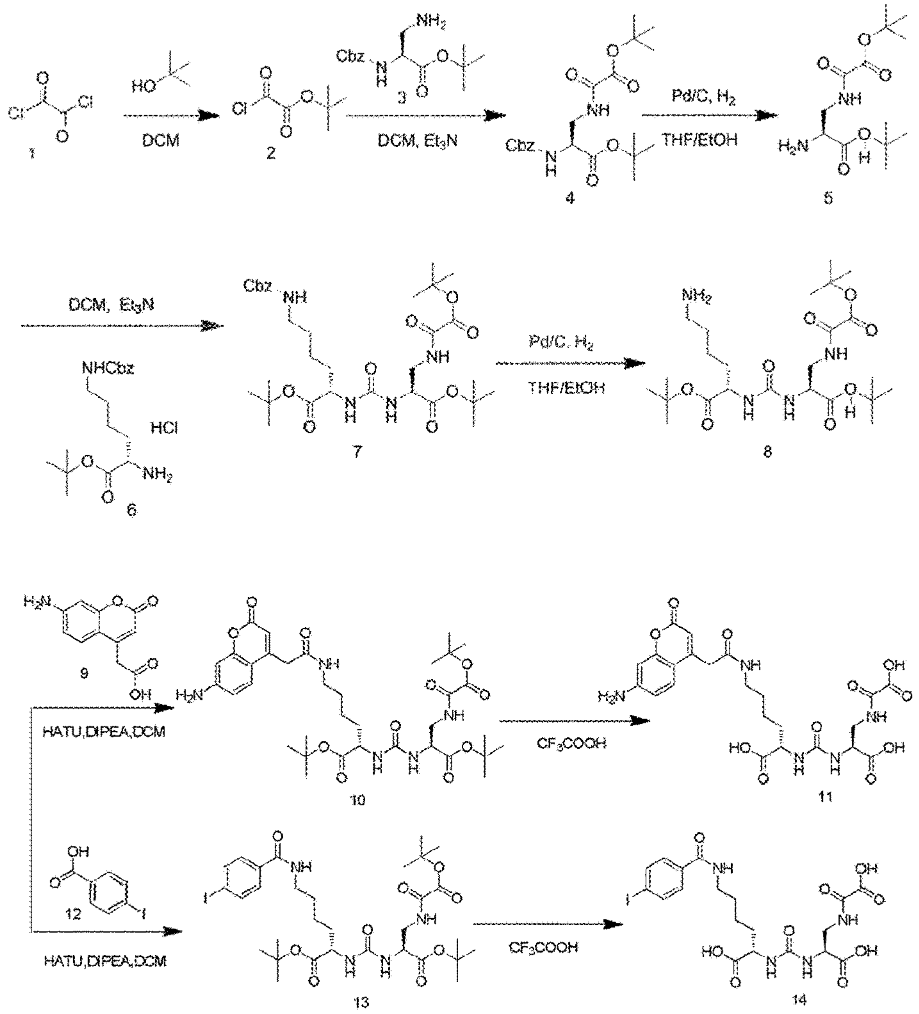
FIG. 4 illustrates the synthetic routes for Compound S1 and Compound S2.

These examples are used to illustrate the synthesis and characterization of Compound S1 and Compound S2. Their synthetic routes are shown in FIG. 4.

(1) Synthesis of Compound 2: tert-butyl 2-chloro-2-oxoacetate

In a 100 mL round bottom flask, oxalyl chloride (1 g, 7.88 mmol) was dissolved in anhydrous dichloromethane (15 mL), and a solution of tert-butanol (584 mg, 7.88 mmol) in anhydrous dichloromethane (15 mL) was slowly added dropwise to the reaction solution under stirring in an ice bath. After the dropwise addition was completed, a reaction was allowed to proceed at room temperature under nitrogen protection for 24 h. The solvent was removed under reduced pressure to obtain a colorless liquid product 2, which was directly used in the next reaction step.

(2) Synthesis of Compound 4: (S)-tert-butyl 2-(((benzyloxy)carbonyl)amino)-3- (2-(tert-butoxy)-2-oxoacetamido)propanoate In a 100 mL round bottom flask, Compound 3 (1 g, 3.40 mmol) was dissolved in anhydrous dichloromethane (20 mL), triethylamine (1.38 g, 13.61 mmol) was added, and a crude solution of Compound 2 (1.29 g, 7.88 mmol) in dichloromethane (15 mL) was added under stirring in an ice bath. A reaction was allowed to proceed at room temperature for 6 h. The solvent was removed under reduced pressure, and the residue was purified by silica gel flash chromatography with a mobile phase of ethyl acetate:n-hexane=0% to 50% (v/v), to give a colorless oily product 4 (1.1 g, 77% yield).

$^1$H NMR (400 MHz, $CDCl_3$) δ7.66 (s, 1H), 7.37-7.29 (m, 5H), 5.82 (d, J=6.8 Hz, 1H), 5.11 (s, 2H), 4.45-4.27 (m, 1H), 3.73-3.65 (m, 2H), 1.53 (s, 9H), 1.45 (s, 9H). $^{13}$C NMR (100 MHz, $CDCl_3$) δ168.87, 159.14, 157.98, 156.29, 136.08, 128.52, 128.21, 128.13, 84.57, 83.33, 67.14, 54.37, 42.14, 27.77. MS calcd. For $C_{21}H_{30}N_2O_7$[M+H]$^+$ 423.2. Found 423.2.

(3) Synthesis of Compound 5: (S)-tert-butyl 2-amino-3-(2-(tert-butoxy)-2-oxoacetamido) propanoate In a 100 mL round bottom flask, Compound 4 (1 g, 2.37 mmol) was dissolved in a mixture of tetrahydrofuran (15 mL) and ethanol (10 mL), palladium on carbon (20 mg) was added, and a reaction was allowed to proceed under stirring at room temperature under hydrogen gas for 10 h. When the reaction was completed as indicated by TLC, the resultant was suction-filtered through diatomaceous earth, washed with ethanol (15 mL) and dichloromethane (15 mL) respectively, the solvent was removed from the filtrate at reduced pressure, and the residue was purified by silica gel flash chromatography with a mobile phase of methanol:dichloromethane=0% to 10% (v/v), to give a colorless gel-like product 5 (580 mg, 85% yield).

$^1$H NMR (400 MHz, $CDCl_3$) δ7.56 (s, 1H), 3.68-3.59 (m, 1H), 3.54-3.46 (m, 1H), 3.41-3.27 (m, 1H), 1.56-1.53 (m, 8H), 1.47 (dd, J=2.6, 1.5 Hz, 9H). $^{13}$C NMR (100 MHz, $CDCl_3$) δ172.70, 159.44, 157.61, 84.44, 82.22, 54.19, 43.07, 27.98, 27.72. MS calcd. For $C_{13}H_{24}N_2O_5$[M+H]$^+$ 289.2. Found 289.2.

(4) Synthesis of Compound 7: (9S,13S)-tri-tert-butyl 3,11,16-trioxo-1-phenyl-2-oxa-4,10,12,15-tetraazahexadecane-9,13,16-tricarboxylate In a 100 mL round bottom flask, triphosgene (56 mg, 0.19 mmol) was dissolved in anhydrous dichloromethane (20 mL), a solution of Compound 6 (200 mg, 0.54 mmol) and triethylamine (219 mg, 2.16 mmol) in anhydrous dichloromethane (15 mL) was slowly added dropwise to the reaction solution under an ice bath. After the dropwise addition was completed, a reaction was allowed to proceed under an ice bath for 2 h.

To the reaction solution, a solution of Compound 5 (156 mg, 0.54 mmol) and triethylamine (164 mg, 1.62 mmol) in anhydrous dichloromethane (10 mL) was slowly added dropwise under an ice bath. After the dropwise addition was completed, a reaction was allowed to proceed at room temperature for 10 h. The solvent was removed from the reaction solution under reduced pressure, and the residue was purified by silica gel flash chromatography with the mobile phase of methanol:dichloromethane=0% to 10% (v/v), to give a white solid crude product 7 (230 mg, 66% yield), which was used directly in the next reaction step.

MS calcd. For $C_{32}H_{50}N_4O_{10}$ [M+H]$^+$ 651.4. Found 651.4.

(5) Synthesis of Compound 8: (S)-tert-butyl 6-amino-2-(34(S)-1-(tert-butoxy)-3-(2-(tert-butoxy)-2-oxoacetamido)-1-oxopropan-2-yl)ureido)hexanoate In a 100 mL round bottom flask, Compound 7 (230 mg, 0.35 mmol) was dissolved in a mixture of tetrahydrofuran (15 mL) and ethanol (10 mL), palladium on carbon (20 mg) was added, and the reaction was allowed to proceed under stirring at room temperature under hydrogen gas for 10 h. When the reaction was completed as indicated by TLC, the resultant was suction-filtered through diatomaceous earth, washed with ethanol (15 mL) and dichloromethane (15 mL) respectively, the solvent was removed from the filtrate at reduced pressure, to obtain a colorless gel-like crude product, which was directly used in the next reaction step.

MS calcd. For $C_{24}H_{44}N_4O_8$ [M+H]$^+$ 517.3. Found 517.3.

(6) Synthesis of Compound $S_1$ (i.e. Compound 11) (45,85)-15-(7-amino-2-oxo-2H-chromen-4-yl)-1,6,14-trioxo-2,5,7,13-tetraazapentadecane-1,4,8-tricarboxylic acid In a 25 mL round bottom flask, Compound 9 (20 mg, 0.09 mmol), HATU (38 mg, 0.1 mmol), DIPEA (47 mg, 0.37 mmol) and Compound 8 (47 mg, 0.09 mmol) were dissolved in anhydrous dichloromethane (20 mL) and stirred at room temperature for 4 h. The solvent was removed from the reaction solution under reduced pressure, and trifluoroacetic acid was added (3 mL), followed by stirring at room temperature for 3 h, the solvent was removed under reduced pressure, and the residue was prepared by reversed C18 HPLC with the mobile phases of acetonitrile (0.1% trifluoroacetic acid) and water (0.1% trifluoroacetic acid), to give compound 11 (12 mg, 24% yield for the two-step reaction) as a white solid.

$^1$H NMR (400 MHz, MeOD) δ7.48 (d, J=8.6 Hz, 1H), 6.67 (d, J=8.4 Hz, 1H), 6.55 (s, 1H), 6.05 (s, 1H), 4.54-4.67 (m, 1H), 4.29-4.26 (m, 1H), 3.68 (s, 2H), 3.37 (s, 2H), 3.24-3.19 (m, 2H), 2.07-2.03 (m, 1H), 1.88-1.83 (m, 1H), 1.71-1.56 (m, 2H), 1.47-1.38 (m, 2H). MS calcd. For $C_{23}H_{27}N_5O_{11}$ [M+H]$^+$ 550.2. Found 550.1.

(7) Synthesis of Compound S2 (i.e. Compound 14) (45,85)-14-(4-iodophenyl)-1,6,14-trioxo-2,5,7,13-tetraazatetradecane-1,4,8-tricarboxylic acid In a 25 mL round bottom flask, Compound 12 (20 mg, 0.08 mmol), HATU (34 mg, 0.09 mmol), DIPEA (42 mg, 0.32 mmol) and Compound 8 (41 mg, 0.08 mmol) were dissolved in anhydrous dichloromethane (20 mL) and stirred at room temperature for 4 h. The solvent was removed from the reaction solution under reduced pressure, and trifluoroacetic acid (3 mL) was added, followed by stirring at room temperature for 3 h. The solvent was removed under reduced pressure, and the residue was prepared by reversed C18 HPLC with the mobile phases of acetonitrile (0.1% trifluoroacetic acid) and water (0.1% trifluoroacetic acid), to obtain compound 14 (10 mg, two-step reaction yield 22%) as a white solid.

$^1$H NMR (400 MHz, MeOD) δ7.71 (d, J=8.5 Hz, 2H), 7.44 (d, J=8.5 Hz, 2H), 4.35 (t, J=6.0 Hz, 1H), 4.16 (dd, J=8.3, 4.8 Hz, 1H), 3.54-3.52 (m, 2H), 3.25 (t, J=6.9 Hz, 2H), 1.97-1.87 (m, 1H), 1.80-1.70 (m, 1H), 1.62-1.47 (m, 2H), 1.38-1.32 (m, 2H). MS calcd. For $C_9H_{23}IN_4O_9$ [M+H]$^+$ 579.0. Found 578.9.

Comparative Examples 1-4 and Example 3

Figure 5:
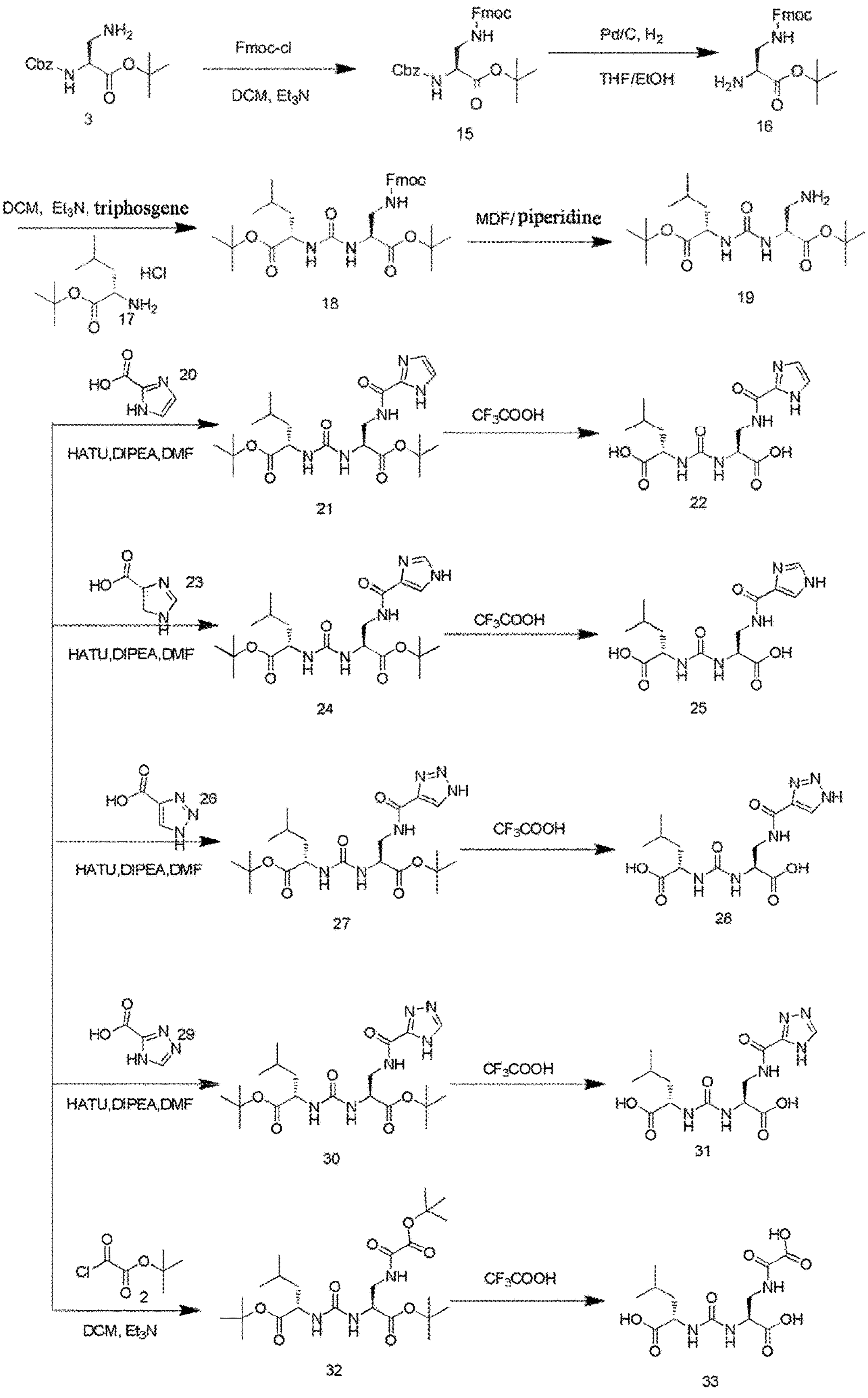
FIG. 5 illustrates the synthetic routes for the comparative compounds DS1-DS4 and Compound S3.

These examples are used to illustrate the synthesis and characterization of the comparative compounds DS1-DS4 and Compound S3. The synthetic routes are shown in FIG. 5.

(1) Synthesis of Compound 15: (S)-tert-butyl 3-((((9H-fluoren-9-yl) methoxy)carbonyl)amino)-2-(((benzyloxy)carbonyl) amino) propanoate In a 25 mL round bottom flask, Compound 3 (1 g, 3.40 mmol) and triethylamine (688 mg, 6.80 mmol) were dissolved in anhydrous dichloromethane (30 mL), and Fmoc-Cl (924 mg, 3.57 mmol) was added slowly. After the addition was completed, the reaction solution was stirred at room temperature for 3 h. When the reaction was completed as indicated by TLC, the solvent was removed from the reaction solution under reduced pressure. The residue was purified by silica gel flash chromatography with the mobile phase of ethyl acetate:petroleum ether=0% to 30% (v/v), to give a colorless gel-like product 15 (900 mg, 51% yield).

$^1$H NMR (400 MHz, $CDCl_3$) δ7.75 (d, J=7.5 Hz, 2H), 7.56 (d, J=7.4 Hz, 2H), 7.38 (t, J=7.4 Hz, 2H), 7.32-7.28 (m, 7H), 5.70 (s, 1H), 5.17 (s, 1H), 5.10 (s, 2H), 4.40-4.35 (m, 2H), 4.19 (t, J=6.8 Hz, 1H), 3.62 (s, 2H), 1.45 (s, 9H). $^{13}$C NMR (100 MHz, $CDCl_3$) δ169.21, 156.61, 156.15, 143.85, 141.31, 136.14, 128.55, 128.24, 128.19, 127.73, 127.10, 125.09, 120.00, 83.11, 67.15, 67.07, 55.07, 47.16, 43.11, 27.93. MS calcd. For $C_{30}H_{32}N_2O_4$ [M+H]$^+$ 517.2. Found 517.3.

(2) Synthesis of Compound 16: (S)-tert-butyl 3-((((9H-fluoren-9-yl)methoxy) carbonyl)amino)-2-aminopropanoate In a 100 mL round bottom flask, Compound 15 (900 mg, 1.74 mmol) was dissolved in a mixture of tetrahydrofuran (25 mL) and ethanol (10 mL), palladium on carbon (30 mg) was added, and a reaction was allowed to proceed under stirring at room temperature under hydrogen gas for 15 h. When the reaction was completed as indicated by TLC, the resultant was suction-filtered through diatomaceous earth, washed with ethanol (15 mL) and dichloromethane (15 mL) respectively, the solvent was removed from the filtrate at reduced pressure, and the residue was purified by silica gel flash chromatography with a mobile phase of methanol: dichloromethane=0% to 10% (v/v), to give a colorless gel-like product 16 (550 mg, yield 83%). MS calcd. For $C_{22}H_{26}N_2O_4$ [M+H]$^+$ 383.2. Found 383.2.

(3) Synthesis of Compound 18: (6S,10S)-tert-butyl 6-(tert-butoxycarbonyl)-1-(9H-fluoren-9-yl)-10-isobutyl-3,8-dioxo-2-oxa-4,7,9-triazaundecan-11-oate In a 100 mL round bottom flask, triphosgene (139 mg, 0.47 mmol) was dissolved in anhydrous dichloromethane (20 mL), a solution of Compound 17 (300 mg, 1.35 mmol) and triethylamine (545 mg, 5.38 mmol) in anhydrous dichloromethane (15 mL) was slowly added dropwise to the reaction solution under an ice bath. After the dropwise addition was completed, a reaction was allowed to proceed under an ice bath for 2 h. To the reaction solution, a solution of Compound 16 (514 mg, 1.35 mmol) and triethylamine (408 mg, 4.03 mmol) in anhydrous dichloromethane (10 mL) was slowly added dropwise under an ice bath. After the dropwise addition was completed, a reaction was allowed to proceed at room temperature for 10 h. The solvent was removed from the reaction solution under reduced pressure, and the residue was purified by silica gel flash chromatography with the mobile phase of methanol:dichloromethane=0% to 10% (v/v), to give a white solid product 18 (620 mg, 77% yield).

$^1$H NMR (400 MHz, $CDCl_3$) δ7.75 (d, J=7.5 Hz, 2H), 7.63 (t, J=7.9 Hz, 2H), 7.39 (t, J=7.4 Hz, 2H), 7.30 (t, J=7.4 Hz, 2H), 5.68 (s, 1H), 5.43 (s, 1H), 5.26 (s, 1H), 4.49 (s, 1H), 4.42-4.17 (m, 4H), 3.64-3.49 (m, 2H), 1.75-1.70 (m, 1H), 1.61-1.56 (m, 1H), 1.51-1.49 (m, 1H), 1.45 (s, 9H), 1.42 (s, 9H), 0.94 (d, J=5.1 Hz, 6H). $^{13}$C NMR (100 MHz, $CDCl_{13}$) δ173.65, 170.21, 157.33, 156.70, 144.03, 141.25, 127.62, 127.08, 125.30, 119.89, 82.76, 81.90, 67.1, 54.37, 52.34, 47.15, 43.79, 42.31, 27.93, 24.85, 22.84, 22.09. MS calcd. For $C_{33}H_{45}N_3O_7$ [M+H]$^+$ 596.3. Found 596.4.

(4) Synthesis of Compound 22 (i.e., Comparative compound DS1): (S)-2-(3-((S)-1-carboxy-2-(1H-imidazole-2-carboxamido)ethyl)ureido)-4-methyl-pentanoic acid In a 25 mL round bottom flask, Compound 18 (70 mg, 0.12 mmol) was dissolved in DMF (3 mL), and piperidine (0.6 mL) was added, followed by stirring at room temperature for 2 h. When the reaction was completed as indicated by TLC, the solvent was removed under reduced pressure to yield a white residue, the residue was dissolved in DMF (2 mL) and added to a reaction solution of Compound 20 (16 mg, 0.14 mmol), DIPEA (61 mg, 0.47 mmol) and HATU (58 mg, 0.15 mmol) in DMF (3 mL), followed by stirring at room temperature for 4 h. The solvent was removed under reduced pressure, and the residue was added to trifluoroacetic acid (3 mL), followed by stirring at room temperature for 2 h. The solvent was removed under reduced pressure, and the residue was prepared by reversed C18 HPLC with the mobile phase of acetonitrile (0.1% trifluoroacetic acid) and water (0.1% trifluoroacetic acid), to give Compound 22 (10 mg, three-step yield: 24%) as a white solid.

$^1$H NMR (400 MHz, MeOD) δ7.51 (s, 2H), 4.60 (dd, J=7.7, 4.7 Hz, 1H), 4.28 (dd, J=9.7, 4.9 Hz, 1H), 3.90 (dd, J=13.6, 4.8 Hz, 1H), 3.71 (dd, J=13.9, 7.8 Hz, 1H), 1.81-1.74 (m, 1H), 1.67-1.49 (m, 2H), 0.97 (dd, J=8.3, 6.6 Hz, 6H). MS calcd. For $C_{14}H_{21}N_5O_6$ [M+H]$^+$ 356.2. Found 356.2.

(5) Synthesis of Compound 25 (i.e., Comparative compound DS2): (S)-2-(3-((S)-1-carboxy-2-(1H-imidazole-4-carboxamido)ethyl)ureido)-4-methyl-pentanoic acid In a 25 mL round bottom flask, Compound 18 (70 mg, 0.12 mmol) was dissolved in DMF (3 mL), and piperidine (0.6 mL) was added, followed by stirring at room temperature for 2 h. When the reaction was completed as indicated by TLC, the solvent was removed under reduced pressure to yield a white residue, the residue was dissolved in DMF (2 mL) and added to a reaction solution of Compound 23 (16 mg, 0.14 mmol), DIPEA (61 mg, 0.47 mmol) and HATU (58 mg, 0.15 mmol) in DMF (3 mL), followed by stirring at room temperature for 4 h. The solvent was removed under reduced pressure, and the residue was added to trifluoroacetic acid (3 mL), followed by stirring at room temperature for 2 h. The solvent was removed under reduced pressure, and the residue was prepared by reversed C18 HPLC with the mobile phase of acetonitrile (0.1% trifluoroacetic acid) and water (0.1% trifluoroacetic acid), to give Compound 25 (12 mg, three-step yield: 29%) as a white solid.

$^1$H NMR (400 MHz, MeOD) δ8.90 (s, 1H), 7.98 (s, 1H), 4.59 (dd, J=7.4, 4.8 Hz, 1H), 4.29 (dd, J=9.7, 4.8 Hz, 1H), 3.85 (dd, J=13.7, 4.6 Hz, 1H), 3.66 (dd, J=13.6, 8.1 Hz, 1H), 1.80-1.73 (m, 1H), 1.65-1.51 (m, 2H), 0.97 (t, J=7.7 Hz, 6H). LRMS calcd. For $C_{14}H_{21}N_5O_6$ $[M+H]^+$ 356.2. Found 356.2.

(6) Synthesis of Compound 28 (i.e., Comparative compound DS3): (S)-2-(3-((S)-1-carboxy-2-(1H-1,2,3-triazole-4-carboxamido)ethyl)ureido)-4-methylpentanoic acid In a 25 mL round bottom flask, Compound 18 (80 mg, 0.13 mmol) was dissolved in DMF (3 mL), and piperidine (0.6 mL) was added, followed by stirring at room temperature for 2 h. When the reaction was completed as indicated by TLC, the solvent was removed under reduced pressure to yield a white residue, the residue was dissolved in DMF (2 mL) and added to a reaction solution of Compound 26 (17 mg, 0.15 mmol), DIPEA (67 mg, 0.52 mmol) and HATU (59 mg, 0.16 mmol) in DMF (3 mL), followed by stirring at room temperature for 4 h. The solvent was removed under reduced pressure, and the residue was added to trifluoroacetic acid (3 mL), followed by stirring at room temperature for 2 h. The solvent was removed under reduced pressure, and the residue was prepared by reversed C18 HPLC with the mobile phase of acetonitrile (0.1% trifluoroacetic acid) and water (0.1% trifluoroacetic acid), to give compound 28 (13 mg, three-step yield: 28% yield) as a white solid.

$^1$H NMR (400 MHz, MeOD) δ8.22 (s, 1H), 4.54 (t, J=5.8 Hz, 1H), 4.30 (dd, J=9.4, Hz, 1H), 3.80 (d, J=3.7 Hz, 2H), 1.81-1.72 (m, 1H), 1.65-1.52 (m, 2H), 0.96 (t, J=6.9 Hz, 6H). $^{13}$C NMR (100 MHz, MeOD) δ175.83, 174.48, 172.75, 161.74, 158.62, 141.51, 52.97, 51.30, 41.08, 40.64, 24.56, 21.98, 20.62. MS calcd. For $C_{13}H_{20}N_6O_6$ $[M+H]^+$ 357.2. Found 357.2.

(7) Synthesis of Compound 31 (i.e., Comparative compound DS4): (S)-2-(3-((S)-1-carboxy-2-(4H-1,2,4-triazole-3-carboxamido)ethyl)ureido)-4-methylpentanoic acid In a 25 mL round bottom flask, Compound 18 (80 mg, 0.13 mmol) was dissolved in DMF (3 mL), and piperidine (0.6 mL) was added, followed by stirring at room temperature for 2 h. When the reaction was completed as indicated by TLC, the solvent was removed under reduced pressure to yield a white residue, the residue was dissolved in DMF (2 mL) and added to a reaction solution of Compound 29 (17 mg, 0.15 mmol), DIPEA (67 mg, 0.52 mmol) and HATU (59 mg, 0.16 mmol) in DMF (3 mL), followed by stirring at room temperature for 4 h. The solvent was removed under reduced pressure, and the residue was added to trifluoroacetic acid (3 mL), followed by stirring at room temperature for 2 h. The solvent was removed under reduced pressure, and the residue was prepared by reversed C18 HPLC with the mobile phase of acetonitrile (0.1% trifluoroacetic acid) and water (0.1% trifluoroacetic acid), to give Compound 31 (15 mg, three-step yield: 31%) as a white solid.

$^1$H NMR (400 MHz, MeOD) δ8.45 (s, 1H), 4.52 (t, J=5.4 Hz, 1H), 4.30 (dd, J=9.4, Hz, 1H), 3.80 (t, J=6.0 Hz, 2H), 1.83-1.69 (m, 1H), 1.66-1.48 (m, 2H), 0.96 (t, J=6.9 Hz, 6H). MS calcd. For $C_{13}H_{20}N_6O_6$ $[M+H]^+$ 357.1. Found 357.2.

(8) Synthesis of Compound 33 (i.e., Compound S3): (S)-2-(3-((S)-1-carboxy-2-(carboxyformamido)ethyl)ureido)-4-methylpentanoic acid In a 25 mL round bottom flask, Compound 18 (50 mg, 0.08 mmol) was dissolved in DMF (3 mL), and piperidine (0.6 mL) was added, followed by stirring at room temperature for 2 h. When the reaction was completed as indicated by TLC, the solvent was removed under reduced pressure to yield a white residue, the residue was dissolved in anhydrous dichloromethane (10 mL), and triethylamine (68 mg, 0.67 mL) was added, then a solution of Compound 2 (41 mg, 0.25 mL) in dichloromethane (3 mL) was added, followed by stirring at room temperature for 4 h. The solvent was removed under reduced pressure, and the residue was added to trifluoroacetic acid (3 mL), followed by stirring at room temperature for 2 h. The solvent was removed under reduced pressure, and the residue was prepared by reversed C18 HPLC with the mobile phase of acetonitrile (0.1% trifluoroacetic acid) and water (0.1% trifluoroacetic acid), to give Compound 33 (10 mg, three-step yield: 36%) as a white solid.

$^1$H NMR (400 MHz, MeOD) δ4.35 (t, J=5.9 Hz, 1H), 4.16 (dd, J=9.6, 5.0 Hz, 1H), 3.53 (d, J=5.9 Hz, 2H), 1.67-1.59 (m, 1H), 1.53-1.37 (m, 2H), 0.83 (t, J=7.3 Hz, 6H). $^{13}$C NMR (100 MHz, MeOD) δ175.82, 172.44, 160.96, 159.12, 158.55, 52.50, 51.28, 41.18, 41.07, 24.57, 21.99, 20.61. MS calcd. For $C_{12}H_{19}N_3O_8$ $[M+H]^+$ 334.1. Found 334.2.

Test Example 1

This test example is used to display the results of the PSMA inhibitory activity tested for each compound and comparative compound.

A LNCaP cell lysate (total protein concentration: 125 μg/mL) was prepared in advance. 25 μL of the cell lysate, 25 μL of the inhibitor and 25 μL of N-acetylaspartylglutamate (NAAG, 16 μM) were incubated together in a 96-well plate (Costar Assay Plate, Cat #. 3925) at 37° C. for 180 min. The amount of glutamate released by hydrolysis of NAAG was measured using an Amplex Red Glutamic Acid Kit (Molecular Probes Inc., Eugene, OR) working solution (50 μL) after incubation for 30 min Fluorescence were measured using Synergy H1 Hybrid Reader (BioTek Instruments, Inc., Winooski, Vermont) at excitation wavelength of 530 nm and emission wavelength of 590 nm. An inhibition curve was plotted by a semi-logarithmic method. ICso values were calculated as the inhibitor concentration at which the enzyme activity was inhibited to 50%. The inhibition constant (Ki) of the enzyme was calculated by the Cheng-Prusof equation. Each experiment was performed in triplicates. Data analysis was performed by GraphPad Prism 7.0 (GraphPad Software, San Diego, California). The results are shown in Table 1 below.

TABLE 1
| PSMA inhibitory activity | | |
|---|---|---|
| No. | Structure of compound | $K_i$ (nM) |
| ZJ-43 | 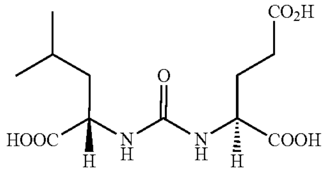 [SMILES: CC(C)C[C@H](NC(=O)N[C@@H](CCC(=O)O)C(=O)O)C(=O)O] | 3.53 |
| Compound S1 | 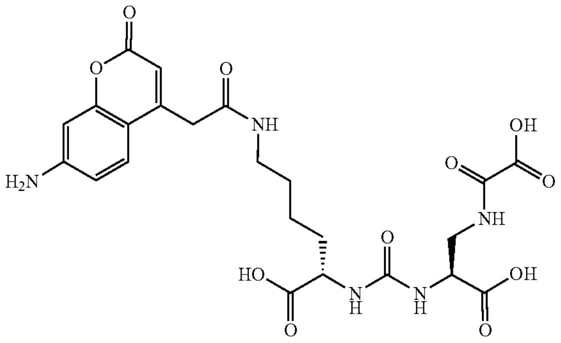 [SMILES: Nc1ccc2c(CC(=O)NCCCC[C@H](NC(=O)N[C@@H](CNC(=O)C(=O)O)C(=O)O)C(=O)O)cc(=O)oc2c1] | 5.96 |
| Compound S2 | 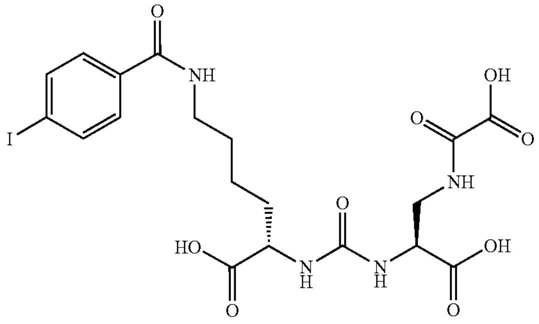 [SMILES: O=C(N[C@@H](CCCCNC(=O)c1ccc(I)cc1)C(=O)O)N[C@@H](CNC(=O)C(=O)O)C(=O)O] | 0.08 |
| Compound S3 | 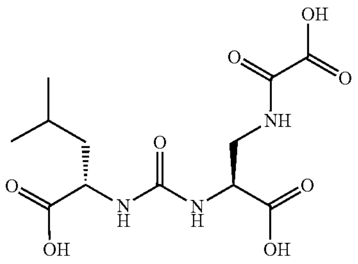 [SMILES: CC(C)C[C@H](NC(=O)N[C@@H](CNC(=O)C(=O)O)C(=O)O)C(=O)O] | 5.69 |
| Comparative Compound DS1 | 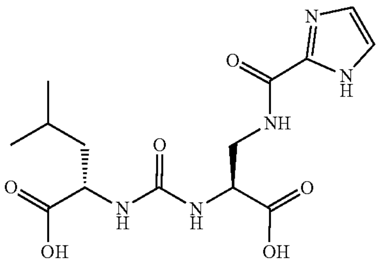 [SMILES: CC(C)C[C@H](NC(=O)N[C@@H](CNC(=O)c1ncc[nH]1)C(=O)O)C(=O)O] | >1000 (10.7% inhibited at 6667 nM) |

TABLE 1-continued

PSMA inhibitory activity

| No. | Structure of compound | $K_i$ (nM) |
|---|---|---|
| Comparative Compound DS2 | 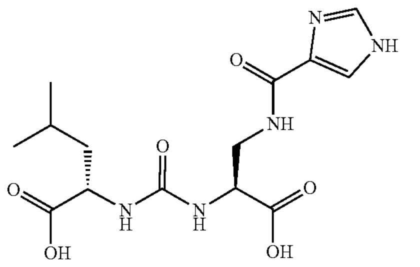 [SMILES: CC(C)C[C@H](NC(=O)N[C@@H](CNC(=O)c1c[nH]cn1)C(=O)O)C(=O)O] | >1000 (20.6% inhibited at 6667 nM) |
| Comparative Compound DS3 | 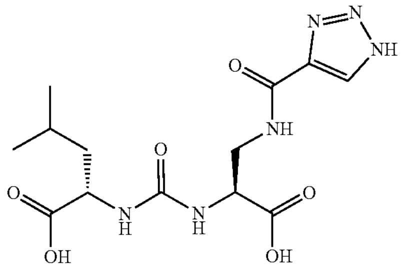 [SMILES: CC(C)C[C@H](NC(=O)N[C@@H](CNC(=O)c1c[nH]nn1)C(=O)O)C(=O)O] | >1000 (47.3% inhibited at 6667 nM) |
| Comparative Compound DS4 | 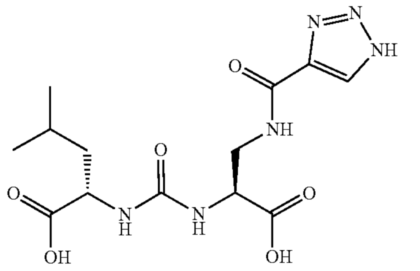 [SMILES: CC(C)C[C@H](NC(=O)N[C@@H](CNC(=O)c1c[nH]nn1)C(=O)O)C(=O)O] | >1000 (24.8% inhibited at 6667 nM) |

As can be seen from Table 1, the PSMA inhibitors of the present disclosure have remarkable PSMA inhibitory activity. In particular, Compound S2 shows an affinity 44 times higher than that of ZJ-43, a highly active PSMA inhibitor known in the art.

Test Example 2

This test example is used to display the results of the flow cytometric analysis with Compound S2.

Figure 6:
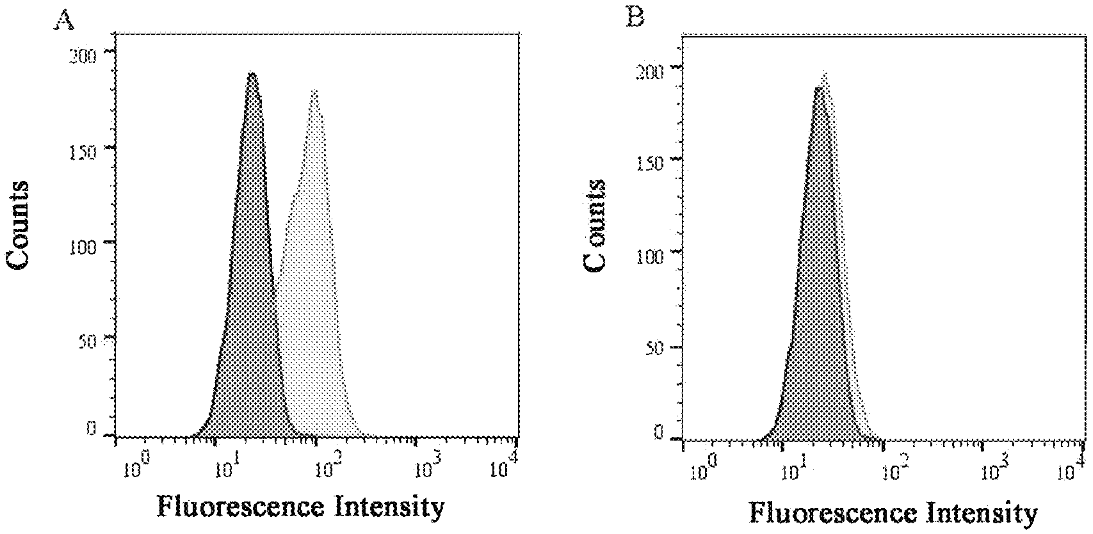
FIG. 6 shows the analysis results of fluorescence activated LNCaP cells. The black area indicates LNCaP cells without dyes, and the blue area indicates LNCaP cells after co-incubation with YC-36. Panel A shows the result when no inhibitor (Compound S2) was added, and Panel B shows the result after 100× inhibitor (Compound S2) was added.

LNCaP cells were diluted to $1\times10^6$/mL with RPMI-1640 (containing 10% FBS). For staining, the cells and 2 μM YC-36 were incubated at room temperature for 1 h, and then washed twice with the same medium. The cells were resuspended in cold PBS. For the inhibition group, the cells were incubated with 2 μM YC-36 and 200 μM Compound S2 for 1 hour at room temperature. The cells were analyzed by BD Influs Cell Sorter (BD Biosciences, San Jose, CA95131, USA) flow cytometry and the FlowJo software, and the results are shown in FIG. 6. The black area (left in Panel A) represents the LNCaP cells without dye, and the blue area (right in Panel A) represents the LNCaP cells after co-incubation with YC-36. Panel A shows the result when no inhibitor (Compound S2) was added, and Panel B shows the result after 100× inhibitor (Compound S2) was added.

YC-36 is a fluorescent molecule having a high affinity for PSMA, and can selectively stain cells with high PSMA expression (Kiess, A. P., et al., Auger Radiopharmaceutical Therapy Targeting Prostate membrane specific antigen. J Nucl Med, 2015. 56(9): p. 1401-1407). The above flow cytometric results showed that Compound S2 significantly inhibited the staining of LNCaP cells with high PSMA expression by YC-36, indicating that Compound S2 specifically binds to PSMA and has a higher affinity than YC-36.

Test Example 3

This Example is used to show the results of fluorescence microscopy imaging with Compound S1 and Compound S2.

Figure 7:
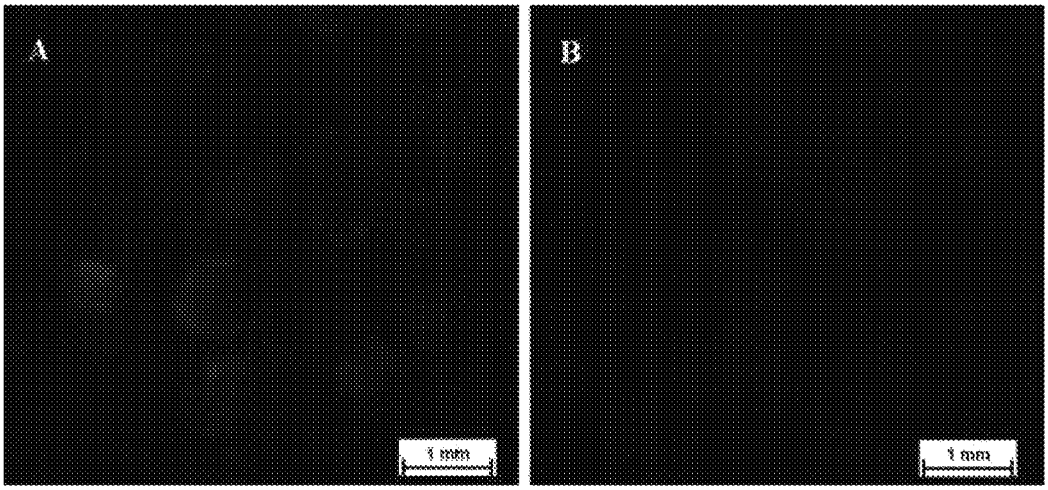
FIG. 7 shows the blue fluorescence images of LNCaP cells. Panel A shows the result when no inhibitor (Compound S2) was added, and Panel B shows the result after 100× inhibitor (Compound S2) was added.

LNCaP cells were diluted to $1\times10^6$/mL with RPMI-1640 (containing 10% FBS). For staining, the cells and 2 μM Compound S1 were incubated at room temperature for 1 h. For the inhibition group, the cells were incubated with 2 μM Compound S1 and 200 μM Compound S2 together for 1 h at room temperature. After the staining was completed, excess dye compound was removed by centrifugation, and the cells were resuspended in cold PBS and blown well, 100 μL of which was taken and added to a 96-well plate, left for several minutes and then observed under a fluorescence microscope. The results are shown in FIG. 7. Panel A shows the result when no inhibitor (Compound S2) was added, and Panel B shows the result after 100× inhibitor (Compound S2) was added.

From the fluorescence microscopy imaging results, it is clear that Compound S2 can significantly inhibit the staining of LNCaP cells by the blue dye Compound S1, which on one hand indicates that Compound S1 stained the cells by specific binding to PSMA, and on the other hand indicates that Compound S2 can significantly inhibit the staining of cells by Compound S1, confirming the higher affinity of Compound S2.

Various embodiments of the present disclosure have been described above, and the foregoing description is exemplary, not exhaustive, and is not limited to the disclosed embodiments. Without departing from the scope and spirit of the illustrated embodiments, many modifications and changes will be apparent to one ordinarily skilled in the art.

What is claimed is:

1. A compound, which a compound having the structure of Formula I or a pharmaceutically acceptable salt thereof, Formula I

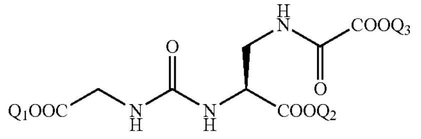

wherein $Q_1$, $Q_2$ and $Q_3$ are each independently H, a negative charge, a metal ion, or a protecting group.

2. A PSMA inhibitor, which is a derivative of the compound of claim 1, wherein the PSMA inhibitor is a derivative formed after one hydrogen atom on the carbon atom marked with * in Formula I is substituted, and after the hydrogen atom is substituted, the carbon atom marked with * has an S-chiral conformation, Formula I

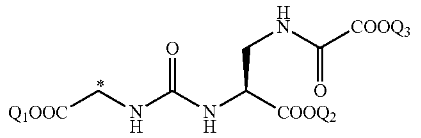

wherein $Q_1$, $Q_2$ and $Q_3$ are each independently H, a negative charge, a metal ion, or a protecting group.

3. A compound, which is at least one of a compound having the structure of Formula II or a pharmaceutically acceptable salt thereof, Formula II

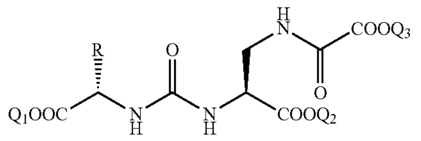

wherein $Q_1$, $Q_2$ and $Q_3$ are each independently H, a negative charge, a metal ion, or a protecting group, and R is a functional group.

4. The compound according to claim 3, wherein the functional group R is a group having one of tracing, delivery, imaging, or therapeutic functions.

5. The compound according to claim 4, which is at least one of a compound having the structure of Formula III or a pharmaceutically acceptable salt thereof, Formula III

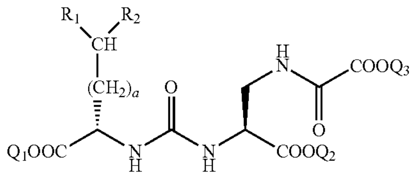

wherein $Q_1$, $Q_2$ and $Q_3$ are each independently H, a negative charge, a metal ion, or a protecting group;

a is an integer selected from 0, 1, 2, 3, 4 or 5;

$R_1$ and $R_2$ are each independently H, a linear or branched $C_1$-$C_4$ alkyl, or a group having the structure of Formula IV;

Formula IV

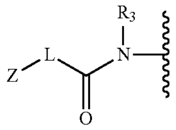

in Formula IV, $R_3$ is H, or a linear or branched $C_1$-$C_4$ alkyl;

L is a chemical bond, or a linear or branched $C_1$-$C_4$ alkyl;

Z is selected from the group consisting of a group containing at least one nuclide suitable for nuclide imaging and/or radiotherapy, and a group containing at least one photosensitive dye suitable for optical imaging and/or photodynamic therapy.

6. The compound according to claim 5, wherein the compound having the structure of Formula III is selected from the group consisting of

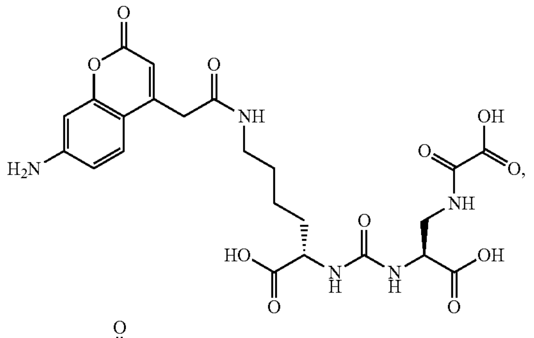

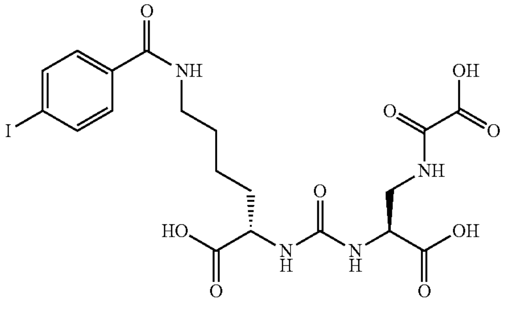

and

-continued

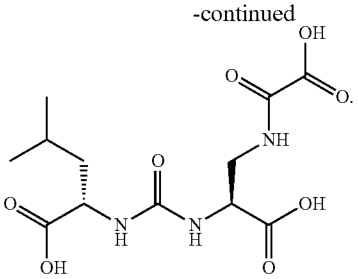

7. A method for imaging or treating one or more types of tumors or cells expressing prostate membrane specific antigen (PMSA) in a subject, comprising contacting the tumors or cells with an effective amount of the compound according to claim 3.

8. The method according to claim 7, wherein the one or more types of tumors or cells expressing PSMA are selected from the group consisting of prostate tumors or cells, metastatic prostate tumors or cells, lung tumors or cells, kidney tumors or cells, liver tumors or cells, glioblastomas, pancreatic tumors or cells, bladder tumors or cells, sarcomas, melanomas, breast tumors or cells, colon tumors or cells, germ cells, pheochromocytoma, esophageal tumors or cells, and gastric tumors or cells.

9. The method according to claim 7, wherein the one or more types of tumors or cells expressing PSMA are in vitro, in vivo, or ex vivo.

10. The compound according to claim 3, wherein the functional group R is selected from the group consisting of a radionuclide-containing group, an optical imaging and/or optical therapeutic group, a group having a magnetic resonance effect, an immunological group, a medication, and a group formed by a delivery system thereof.

11. The compound according to claim 10, wherein the medication comprises at least one of a chemical medication, a nucleic acid medication, or a protein medication.

12. The compound according to claim 11, wherein the nucleic acid medication comprises an siRNA medication.

13. The compound according to claim 10, wherein the radionuclide is selected from the group consisting of $^{18}$F, $^{11}$C, $^{68}$Ga, $^{124}$I, $^{89}$Zr, $^{64}$Cu, $^{86}$Y, $^{99}$mTc, $^{111}$In, $^{123}$I, $^{90}$Y, $^{125}$I, $^{67}$Ga, $^{131}$I, $^{177}$Lu, $^{211}$At, $^{153}$Sm, $^{186}$Re, $^{188}$Re, $^{67}$Cu, $^{212}$Pb, $^{225}$Ac, $^{213}$Bi, $^{212}$Bi, and $^{212}$Pb.

14. The compound according to claim 5, wherein Z is selected from the group consisting of a substituted or unsubstituted $C_6$-$C_{16}$ aryl and a substituted or unsubstituted $C_3$-$C_{16}$ heteroaryl.

15. The compound according to claim 14, wherein the substitution is at least one of a halogen substitution, a linear or branched $C_1$-$C_4$ alkyl substitution, an amino substitution, or a carbonyl substitution.

* * * * *